(12) United States Patent
Liu et al.

(10) Patent No.: US 6,989,142 B2
(45) Date of Patent: Jan. 24, 2006

(54) PRECIPITATED CALCIUM CARBONATE

(75) Inventors: Sung-Tsuen Liu, Aberdeen, MD (US); Michel J. Martin, Plainsboro, NJ (US); William C. Fultz, Rising Sun, MD (US); Patrick D. McGill, Darlington, MD (US)

(73) Assignee: J. M. Huber Corporation, Edison, NJ (US)

( * ) Notice: Subject to any disclaimer, the term of this patent is extended or adjusted under 35 U.S.C. 154(b) by 258 days.

(21) Appl. No.: 10/365,992

(22) Filed: Feb. 13, 2003

(65) Prior Publication Data

US 2004/0161388 A1   Aug. 19, 2004

(51) Int. Cl.
*A61K 7/16* (2006.01)
*C01B 31/24* (2006.01)
*C01F 5/24* (2006.01)
*C01F 11/18* (2006.01)

(52) U.S. Cl. .................. 424/49; 424/687; 423/158; 423/165; 423/200; 423/224; 423/230; 423/266; 423/419.1; 423/430; 423/432

(58) Field of Classification Search .................. 424/49, 424/687; 423/158, 165, 200, 224, 230, 266, 423/419.1, 430, 432
See application file for complete search history.

(56) References Cited

U.S. PATENT DOCUMENTS

| | | | | |
|---|---|---|---|---|
| 5,120,521 A | * | 6/1992 | Ebinuma et al. | 423/432 |
| 5,695,733 A | * | 12/1997 | Kroc et al. | 423/432 |
| 6,808,700 B2 | * | 10/2004 | Kiji et al. | 424/49 |

* cited by examiner

*Primary Examiner*—Frederick Krass
(74) *Attorney, Agent, or Firm*—Carlos Nieves; David Mitchell Goodrich; William Parks

(57) ABSTRACT

An abrasive precipitated calcium carbonate is provided that provides excellent cleaning properties without being excessively abrasive or damaging to gums or tooth surfaces. The abrasive, precipitated calcium carbonate has a primary particle size of about 1 $\mu$m to about 4 $\mu$m, and an aggregate size of about 3 $\mu$m to about 10 $\mu$m. Also disclosed is a method for forming calcium carbonate comprising the steps of: providing a reaction medium; introducing carbon dioxide and the calcium hydroxide slurry simultaneously into a reaction medium to form calcium carbonate while maintaining constant pH during calcium carbonate precipitation; and optionally drying the calcium carbonate slurry to form a dried calcium carbonate product. Also disclosed is a dentifrice containing the aforementioned abrasive, precipitated calcium, and one or more ingredients selected from the group consisting of humectants, thickening agents, binders, gums, stabilizing agents, antibacterial agents, fluorides, sweeteners, and surfactants.

11 Claims, 3 Drawing Sheets

PRECIPITATED CALCIUM CARBONATE

BACKGROUND OF THE INVENTION

Synthetic precipitated calcium carbonate ("PCC") is currently used as an additive in a wide variety of consumer products, such as dentifrice products, foods and food supplements, plastics and elastomers, cosmetics, and paper. PCC can be cleanly and conveniently produced in a precipitation reaction by reacting aqueous $Ca(OH)_2$ ("milk of lime") with carbon dioxide with water being generated as a by-product. In products such as food and foodstuffs, calcium carbonate is useful not only because it supplies the body with an essential nutrient (calcium), but also serves as a conditioner to prevent caking in food powders.

In addition to food products, PCC products are also widely used in dentifrices, particularly toothpastes, where they function as both abrasives and fillers. Because of this functional versatility and because PCCs, when compared to other dentifrice abrasives such as silica and dicalcium phosphate, are much less expensive, there is a strong desire among toothpaste and dentifrice formulators to include them in their products by substituting them for more expensive dentifrice ingredients.

However, while PCC has the aforementioned advantages, it can also be somewhat difficult to prepare calcium carbonate material to have the combination of properties that make it suitable for use in dentifrices. It has been previously noted that the dentifrice-relevant properties of a calcium carbonate material are strongly correlated to its morphology and particle size. For example, scalenohedral-shaped calcium carbonate particles tend to have small particle sizes and provide relatively insignificant cleaning effectiveness. On the other hand, large rhombohedral-shaped (sometimes referred to as "cubic") calcium carbonate particles have increased cleaning and abrasive benefits, but often abrade all too well: their abrasiveness leading to a concern for possible damage to teeth and gums.

Thus, calcium carbonate material must be sufficiently abrasive to effectively clean, but must not be so excessively abrasive that it may damage tooth and soft tissue surfaces. Given the foregoing there is a continuing need for PCC material that improves cleaning performance when included in a dentifrice preparation, while not also being excessively abrasive that it may damage the teeth or gums.

BRIEF SUMMARY OF THE INVENTION

The invention includes an abrasive, precipitated calcium carbonate having a primary particle size of about 1 μm to about 4 μm, and an aggregate size of about 3 μm to about 10 μm.

The invention also includes a method for forming calcium carbonate comprising the steps of: providing a reaction medium; introducing carbon dioxide and the calcium hydroxide slurry simultaneously into a reaction medium to form calcium carbonate while maintaining constant pH during calcium carbonate precipitation; and optionally drying the calcium carbonate slurry to form a dried calcium carbonate product.

The invention also includes a dentifrice containing an abrasive, precipitated calcium carbonate, which has a primary particle size of about 1 μm to about 4 μm, and an aggregate size of about 3 μm to about 10 μm; and one or more ingredients selected from the group consisting of humectants, thickening agents, binders, gums, stabilizing agents, antibacterial agents, fluorides, sweeteners, and surfactants.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
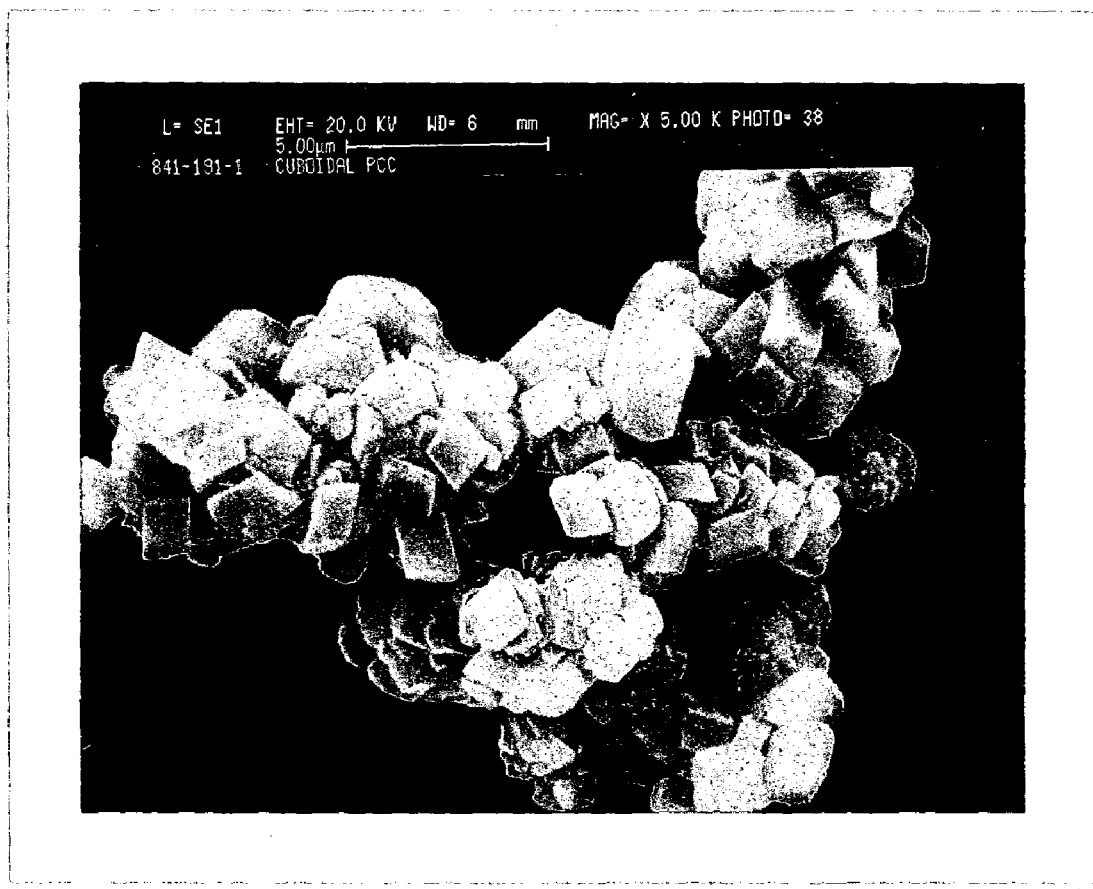
FIG. 1 is a SEM photomicrograph of the cubic PCC prepared as in Example 1, showing PCC aggregates having a size of about 9 μm and primary particles having a size of 1–2 μm.

All parts, percentages and ratios used herein are expressed by weight unless otherwise specified. All documents cited herein are incorporated by reference. The following describes preferred embodiments of the present invention, which provides calcium carbonate for use in dentifrices, such as toothpastes. While the optimal use for this calcium carbonate is in dentifrices, this calcium carbonate may also be used in a variety of other consumer and industrial products. "Calcium carbonate" is used herein to refer specifically to precipitated calcium carbonate ("PCC").

By "dentifrice" it is meant oral care products such as, without intending to be limiting, toothpastes, tooth powders, chewing gums and denture creams.

By "primary particle size" it is meant the size of individual particles, which may be bound to each other to form aggregates, as estimated from visual inspection of a SEM photomicrograph.

By "particle aggregate size" it is meant a group of primary particles bound to each other that cannot be separated by low-energy comminution.

By "particle agglomerate size" it is meant a group of aggregates loosely bound to each other that may be separated by low-energy comminution.

By "viscosity build" it is meant increasing dentifrice viscosity as measured by a Brookfield viscometer and is expressed in centipoise (cps).

By "cubic precipitated calcium carbonate" or "(c-PCC)" it is meant a crystal structure in which the axes of the crystal structure are formed at substantially right angles and are of substantially equal size.

The present invention relates to precipitated calcium carbonate, which provides excellent cleaning properties without being excessively abrasive or damaging to gums or tooth surfaces when included within a toothpaste or dentifrice. Because of their effective dental cleaning performance, and combined with their relatively low-cost, these calcium carbonate materials are particularly useful for formulating dentifrices, particularly toothpastes.

To ensure good cleaning performance a sufficient amount of abrasive calcium carbonate should be added to a dentifrice or toothpaste composition so that the radioactive dentin abrasion ("RDA") value of the toothpaste is between about 50 and 200. At a RDA of less than 50, the cleaning benefits of the toothpaste will be minimal, while at a RDA of greater than 200, there is increasing risk that the toothpaste will be so abrasive that it may damage the tooth dentin along the gum line. Most commercial toothpaste products today have a RDA in the range of 50 to 150, with the average being around 100. Preferably, the dentifrice should have a RDA value of at least about 50, such as between 70 and 120, such as between 90 and 110. Methods for measuring the RDA values of a toothpaste will be discussed in greater detail below.

Another measure of the cleaning effectiveness of a dentifrice or toothpaste composition is expressed in the Pellicle Cleaning Ratio ("PCR"), which measures the ability of a dentifrice composition to remove pellicle film from a tooth under fixed brushing conditions. The higher the measured PCR, the greater the cleaning performance, so accordingly a toothpaste formulator wishes to maximize the measured PCR. However, because of the roughly linear relationship between RDA and PCR, a formulator has to balance the acceptable RDA level with the resulting PCR value.

It has long been known that the RDA and PCR of a toothpaste or dentifrice is dependent on both the hardness of the abrasive and the concentration of the abrasive in the toothpaste. The hardness of the abrasive is itself dependent on many factors such as the intrinsic material hardness, as well as particle size and shape. By the present invention it has also been determined that the hardness of the abrasive is affected by the size of the calcium carbonate aggregates (these aggregates are discussed in greater detail below). By controlling the primary particle size and the aggregate size of these precipitated calcium carbonate abrasives, these materials have excellent abrasion performance without being harsh to teeth and gum surfaces. Specifically, the calcium carbonate material of the present invention has a primary particle size of about 1 $\mu$m to about 4 $\mu$m, with the primary particles themselves capable of forming particle aggregates of a size of about 3 $\mu$m to about 10 $\mu$m. Calcium carbonate material with these characteristics is obtained by: (1) controlling the pH of the reaction mixture (also referred to herein as the reactor media) during the precipitation process, especially during the stage of the precipitation reaction where lime slurry is being added; and (2) judiciously milling the calcium carbonate product of the reaction. Processes for making the present calcium carbonate material are discussed in greater detail, below.

A dentifrice or toothpaste composition incorporating calcium carbonate material having these characteristics has excellent cleaning performance without being excessively abrasive. Thus, this cleaning-effective calcium carbonate material is useful for making dentifrice compositions, and yet at the same time is relatively soft and not excessively abrasive to teeth and tissue surfaces.

Typically, precipitated calcium carbonate is prepared by exposing calcium hydroxide slurry (i.e., milk of lime or slaked lime) to a carbonation reaction. This may be done by injecting carbon dioxide gas into a reaction vessel containing aqueous calcium hydroxide slurry. The product of this carbonation reaction, precipitated calcium carbonate, exists in three primary crystalline forms: calcite, aragonite and vaterite, and there are many different polymorphs (crystal habits) for each of these crystalline forms. Calcite has a trigonal crystal structure with typical crystal habits such as scalenohedron, rhombohedron, hexagonal prism, pinacoid, cubic, and prismatic. Aragonite is an orthorhombic structure with typical crystal habits of twinned hexagonal prismatic crystals, as well as a diverse assortment of thin elongated prismatic, curved bladed, steep pyramidal (spiked), chisel shaped crystals, branching tree, and coral or worm-like delicate form called flos ferri. Vaterite is a hexagonal structure for which the most typical crystal habit is spherical. Calcite is the most stable calcium carbonate form, while aragonite is metastable at normal surface temperatures and pressures, and vaterite is unstable.

In the present invention, the calcium carbonate material has a calcite crystalline form and essentially a cubic crystal structure. As mentioned above, the primary particle size of the calcium carbonate is preferably between about 1 $\mu$m to about 4 $\mu$m. These primary particles themselves may come together and, through covalent bonding to one another, form aggregates having a particle size of between about 3 $\mu$m to about 10 $\mu$m. These aggregates are characterized in that the constituent particles that compose the aggregates can only be separated from one another by high-energy comminution (or milling). High-energy comminution such as media milling (e.g., ball milling, bead milling), may separate some of the primary particles from the aggregate and one another. Low-energy comminution (or milling) includes fluid milling techniques, air-jet milling, pendulum milling, and hammer milling and other such techniques known to a person of ordinary skill in the art. Such low-energy comminution cannot separate the constituent particles of the aggregates either from the aggregate or from each other. Aggregate formations are shown in the SEM micrograph of FIG. 1.

These aggregates can in turn come together and, through electrostatic bonding, form loosely-bonded agglomerates. In contrast to the aforementioned aggregates, these agglomerates are characterized by the fact that they can be separated from each other by low-energy comminution.

As mentioned above, the present calcium carbonate provides excellent cleaning performance without being excessively abrasive. Another important characteristic of the present calcium carbonate material is its color. In order to be acceptable to consumers, an abrasive for use in dentifrices should be sufficiently white so as to not impart any undesirable off-color tint to the final dentifrice or toothpaste product. It has been found that the iron content of the precipitated calcium carbonate can deleteriously affect the product's color, and accordingly it is preferred that the iron content of the calcium carbonate abrasive be less than 400 ppm $Fe_2O_3$, such as less than 200 ppm $Fe_2O_3$.

Additionally, the calcium carbonate of the present invention has a Brass Einlehner abrasion value of less between about 8 mg loss/100,000 rev. to about 15 mg loss/100,000 rev.

In addition to the aforementioned characteristics, the present calcium carbonate material also provides good viscosity build, meaning that when included in a dentifrice composition, the composition has a viscosity that makes it convenient for a consumer's use. This viscosity build performance can itself be correlated with the oil absorption characteristics of the calcium carbonate material—higher oil absorption means improved viscosity build performance.

Calcium carbonate of the present invention is prepared according to the following process. In this process, a reaction media, (e.g., water) is charged into a reactor, such as a reactor equipped with mixing means adequate to ensure a homogeneous mixture, then carbon dioxide gas ($CO_2$) and lime slurry, $Ca(OH)_2$, slurry are simultaneously added to the reactor media. The lime slurry is prepared by adding CaO to water to prepare a lime slurry having a concentration of 10 wt % to 20 wt % $Ca(OH)_2$. The rate of addition of the $CO_2$ gas and the rate of addition of the lime slurry are adjusted so that the pH of the reactor media remains between 8–12 during the addition of the lime slurry, and within this 8–12 pH range, the pH of the reactor media does not vary by more than 1 pH unit throughout the period when lime slurry is being added into the reactor (or reaction) media. Thus, for example, during the precipitation reaction the pH will vary within a range such as 8–9, 8.5–9.5, 9–10, 11–12, etc. (The pH of the reaction media can be adjusted by adjusting the rate of addition of the $CO_2$ gas and the lime slurry. Increasing the rate of addition of the $CO_2$ gas relative to the lime slurry decreases the pH of the reaction media, while increasing the rate of addition of the lime slurry relative to the $CO_2$ gas increases the pH of the reaction media.) Overall, the rate of $CO_2$ gas and lime slurry addition is dependent on the reactor size and should be adjusted so as to complete the batch in a reasonable time, such as about 30 minutes to about 180 minutes.

By regulating the pH of the reaction media so it does not vary by more than 1 pH unit throughout the period when lime slurry is being added, and by keeping the overall pH level within the pH range of 8–12, then calcium carbonate particles having the primary particle size and aggregate particle size dimensions mentioned above are obtained. The primary particle size and aggregate particle size dimensions may be further refined to lie within the desirable range by subjecting the calcium carbonate product to wet milling as discussed below.

The reaction of CaO with water ("slaking") is exothermic, so the slaked lime can be used immediately or allowed to cool to room temperature. After all of the lime slurry that is desired to be added to the reactor is added, the $CO_2$ gas addition is continued until the reactor media is lowered to about pH 7, indicating all the lime slurry has been reacted with the $CO_2$ gas to form calcium carbonate. This calcium carbonate is then filtered. The calcium carbonate may be used in this wet form or further processed.

The filtered calcium carbonate may then be processed in either of two methods. In a first method, the calcium carbonate is dried by any conventional means, such as spray drying. After drying, calcium carbonate may then be reslurried in water and wet-milled by any conventional milling system, such as any high-energy milling method.

Alternatively, in a second method, the filtered calcium carbonate is milled by any conventional wet milling system before it is dried. Any suitable wet milling or high-energy milling method may be used. After being wet-milled the calcium carbonate is then optionally dried.

Regardless of which milling method is used, the milling should be performed so as to obtain an aggregate size of about 3 $\mu$m to about 10 $\mu$m.

This abrasive, precipitated calcium carbonate may then be incorporated into a dentifrice composition, e.g., toothpaste. Typical levels of calcium carbonate abrasives are from about 30 wt % to about 50 wt % of a toothpaste composition, such as from about 40 wt % to about 45 wt %. In addition, the inventive c-PCC abrasive could be used in conjunction with other abrasive materials, such as PCC, precipitated silica, silica gel, and other suitable abrasive materials known to a person of ordinary skill in the art.

The dentifrice may also contain several other ingredients such as humectants, thickening agents, (also sometimes known as binders, gums, or stabilizing agents), antibacterial agents, fluorides, sweeteners, and surfactants.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds. Typical levels of humectants are from about 20 wt % to about 30 wt % of a toothpaste composition.

Thickening agents are useful in the dentifrice compositions of the present invention to provide a gelatinous structure that stabilizes the toothpaste against phase separation. Suitable thickening agents include silica thickener, starch, glycerite of starch, gum karaya (sterculia gum), gum tragacanth, gum arabic, gum ghatti, gum acacia, xanthan gum, guar gum, veegum, carrageenan, sodium alginate, agar-agar, pectin, gelatin, cellulose, cellulose gum, carboxymethyl cellulose, hydroxyethyl cellulose, hydroxypropyl cellulose, hydroxymethyl, hydroxymethyl carboxypropyl cellulose, methyl cellulose, ethyl cellulose, sulfated cellulose, as well as mixtures of these compounds. Typical levels of binders are from about 0 wt % to about 15 wt % of a toothpaste composition.

Antibacterial agents may be included to reduce the presence of microorganisms to below known harmful levels. Suitable antibacterial agents include benzoic acid, sodium benzoate, potassium benzoate boric acid phenolic compounds such as betanapthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride, cetylpyridinium bromide. If present, the level of antibacterial agent is preferably from about 0.1 wt % to about 5 wt % of the toothpaste composition.

Sweeteners may be added to the toothpaste composition to impart a pleasing taste to the product. Suitable sweeteners include saccharin (as sodium, potassium or calcium saccharin), cyclamate (as a sodium, potassium or calcium salt), acesulfane-K, thaumatin, neohisperidin dihydrochalcone, ammoniated glycyrrhizin, dextrose, levulose, sucrose, mannose, and glucose.

The toothpaste will also preferably contain fluoride salts to prevent the development and progression of dental caries. Suitable fluoride salts include sodium fluoride, potassium fluoride, zinc fluoride, stannous fluoride, zinc ammonium fluoride, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and sodium monofluorophosphate. Typical levels of fluoride salts are from about 0.1 wt % to about 5 wt %.

Condensed phosphates may be one or a combination of tetrasodium pyrophosphate, tetrapotassium pyrophosphate, disodium dihydrogen pyrophosphate, trisodium monohydrogen pyrophosphate, pentasodium tripolyphosphate and sodium polymetaphosphate, singly or in combinations thereof.

Surfactants may also be included as additional cleansing and foaming agents, and may be selected from anionic surfactants, zwitterionic surfactants, nonionic surfactants, amphoteric surfactants, and cationic surfactants. Anionic surfactants are preferred, such as metal sulfate salts, such as sodium lauryl sulfate.

The dentifrices disclosed herein may also have a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, whitening agents and preservatives.

Finally, water provides the balance of the composition in addition to the additives mentioned. The water is preferably deionized and free of impurities. The dentifrice will preferably comprise from about 20 wt % to about 35 wt % of water.

The invention will now be described in more detail with respect to the following, specific, non-limiting examples.

EXAMPLE 1

Precipitated c-PCC material was prepared in accordance with the present invention as follows. Lime was slaked in a container by adding 6868 g CaO to water to make a 14.8 wt % lime slurry. The lime was obtained from Companhia Cimento Portland Itau, Arcos, Brazil(Itau), and contained 186 ppm $Fe_2O_3$ and 39 ppm Mn. Subsequently, $CO_2$ gas, at a rate of 25 l/min, and the 14.8 wt % lime slurry were introduced simultaneously into a reactor equipped with a mechanical stirrer and containing 4 liters of water. The lime slurry pump addition rate was adjusted so as to maintain the reactor batch at a pH of between 8.0 and 9.0. After the addition of the lime slurry to the reactor batch was completed, the $CO_2$ gas addition was continued for about 2 more minutes (or until the reaction slurry reached a pH of 7.0, indicating the reaction was complete). The reaction was carried out at room temperature (25° C.). The resultant c-PCC slurry was filtered on a buchner funnel and dried overnight in a 105° C. oven to form particulate calcium carbonate. FIG. 1 is a SEM micrograph of the calcium carbonate powder prepared according to Example 1. Shown in FIG. 1 are calcium carbonate aggregates, with these aggregates in turn being constituted of primary particles of calcium carbonate. The physical properties of Example 1 c-PCC are given in Table II below.

EXAMPLE 2

The steps described above in Example 1 were repeated using a different source of lime. The lime used this time was available from Beachville Lime Limited, Ontario, Canada. This lime contained 806 ppm $Fe_2O_3$ and 109 ppm Mn. Physical properties of Example 2 cubic PCC are given in Table II below.

EXAMPLE 3

The steps described above in Example 1 were followed, except that the slaked lime slurry was allowed to cool to room temperature before being added simultaneously with the $CO_2$ gas to the water-containing reactor. Physical properties of Example 3 c-PCC are given in Table II below.

EXAMPLE 4

The procedure of example 1 was followed, except the reactor was maintained at 70° C., instead of room temperature (25° C.), during the precipitation reaction and the lime slurry pumping rate was such as required to maintain the reactor media at a pH of 11–12. Physical properties of Example 4 c-PCC are given in Table II below.

EXAMPLES 5–7

Figure 3:
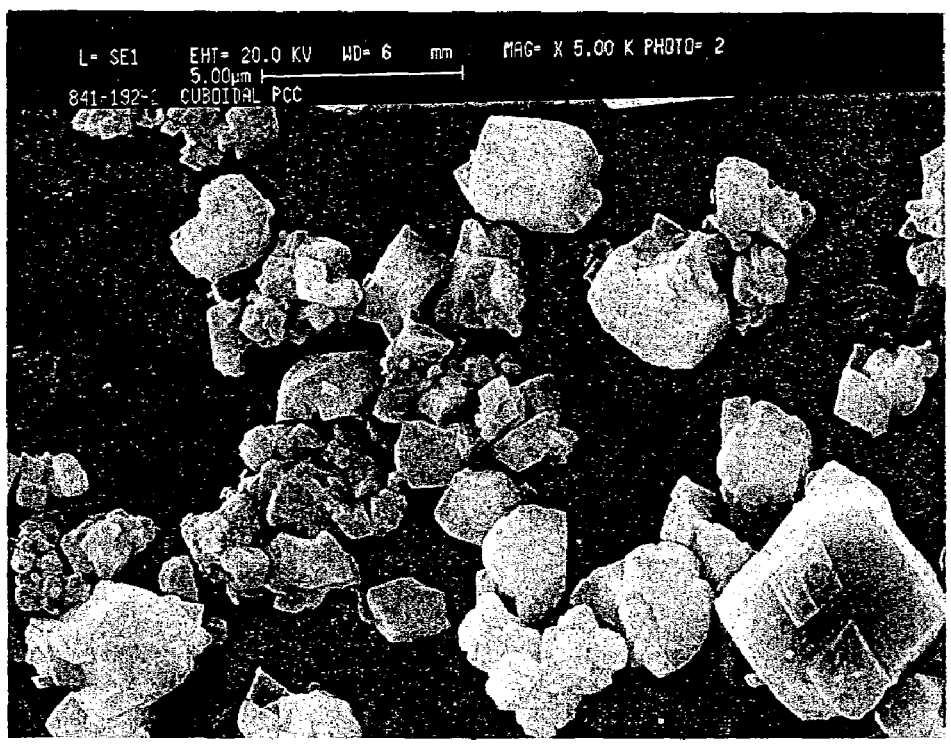
FIG. 3 is a SEM photomicrograph of cubic PCC as prepared and milled in Example 5, showing PCC aggregates having an aggregate size of about 4 μm.

In these examples, the large (9–11 μm) aggregate size c-PCC product of Example 3 was slurried in water to a specified solids content and then milled in a horizontal type media mill (1.5 liter Premier Bead Mill, model HML-1.5, Lightnin, Inc., Reading, Pa.) under the conditions listed below in Table I. The mill was loaded at 80% capacity with 0.8–1.0 micron zirconia media beads having a specific gravity of 3.7. The milling variables controlled were rotation speed (rpm) and retention time (sec). The milled calcium carbonate powder of Example 5 is shown in the micrograph of FIG. 3.

TABLE I

Milling Conditions

| | Starting Material | % Solids | Rotation Speed (rpm) | Retention Time (sec.) |
|---|---|---|---|---|
| Example 5 | Example 3 | 12.9 | 1600 | 30 |
| Example 6 | Example 3 | 9 | 1200 | 20 |
| Example 7 | Example 3 | 14.5 | 1200 | 20 |

COMPARATIVE EXAMPLE 1

Figure 2:
FIG. 2 is a SEM photomicrograph of the cubic PCC prepared as in Comparative Example 1, showing a primary particle size of about 7 to about 9 μm.

In this comparative example, large particle size, cubic calcium carbonate was prepared by first separately preparing 0.75 molar solutions of calcium chloride and sodium carbonate from reagent grade $CaCl_2$ and $Na_2CO_3$. The calcium chloride solution was poured quickly into an equal volume of sodium carbonate solution, while mixing with an arrow mixer. Initially, the solution gels, but with stirring maintained, the gel converts in 30 minutes or less into a white crystalline precipitated calcium carbonate that is in an unstable vaterite form or a mixture of vaterite and calcite. This resulting calcium carbonate is then aged for 1 day to allow the unstable vaterite to completely convert to a stable form of calcite calcium carbonate. After the conversion is completed (conversion is confirmed with X-ray diffraction) the calcite product is filtered, washed to a filtrate conductivity of 500 μS or less to remove by-product salt and then dried in an oven at 105° C. overnight. FIG. 2 is a micrograph showing primary particles of the calcium carbonate material prepared according to Comparative Example 1. Physical properties of Comparative Example 1 product are given in Table II.

COMPARATIVE EXAMPLE 2

Comparative example 2 illustrates a method to prepare conventional scalenohedral precipitated calcium carbonate (s-PCC). First, a 19.2 wt. % lime slurry is prepared by slaking calcium oxide (Beachville) in water containing 0.3% ethylenediamine tetraacetic acid (EDTA). The lime slurry is then diluted to 12 wt. % solids with ice water. To a 5-gallon reactor equipped with mechanical stirrer was added 18,333 g of the 12% lime slurry followed by the introduction of carbon dioxide gas at a rate of 9.4 l/min. The initial reaction temperature was 8.5° C. and the initial pH was greater than 12. There was no temperature control during the reaction. The reaction is completed when the reaction mixture reached pH 7. The final reaction mixture temperature was 49° C. The resultant PCC slurry was filtered and then oven dried overnight at 105° C.

After being prepared as set forth above, several properties of the calcium carbonate were measured, including aggregate size, primary particle size, Einlehner abrasion and iron oxide and manganese content. The methods for measuring these physical properties will now be described in greater detail.

Primary particle size was estimated by visually comparing the sizes of cubic particles to a micron marker on a SEM photomicrograph taken at 5 kX. Individual cubic particles are attached to one another to form aggregates. It is the size of the individual particles that is recorded.

The median particle size of the aggregates was measured by a Sedigraph particle size analyzer (Model 5100), manufactured by Micrometrics Instrument Corp., Norcross, Ga.). This is a sedimentation type instrument, which uses Stokes Law in determining the equivalent spherical particle diameters. The use of such equipment to determine particle size is well within the capabilities of a person of ordinary skill in the art.

The Brass Einlehner (BE) Abrasion value was measured through the use of an Einlehner AT-1000 Abrader. In this test, a Fourdrinier brass wire screen is weighed and exposed to the action of a 10% aqueous calcium carbonate suspension for a fixed number of revolutions, and the amount of abrasion is then determined as milligrams brass lost from the Fourdrinier wire screen per 100,000 revolutions. Disposable supplies required for this test (brass screens, wear plates and PVC tubing) are available from Duncan Associates, Rutland, Vt. and sold as an "Einlehner Test Kit". Specifically, brass screens (Phosphos Bronze P.M.) were prepared by washing in hot, soapy water (0.5% Alconox) in an ultrasonic bath for 5 minutes, then rinsed in tap water and rinsed again in a beaker containing 150 ml water set in an ultrasonic bath. The screen is rinsed again in tap water, dried in an oven set at 105° C. for 20 minutes, cooled in a desiccator and weighed. Screens were handled with tweezers to prevent skin oils from contaminating the screens. The Einlehner test cylinder is assembled with a wear plate and weighed screen (red line side down—not abraded side) and clamped in place. The wear plate is used for about 25 tests or until worn badly; the weighed screen is used only once.

Next, a 10% calcium carbonate slurry, prepared by mixing 100 g calcium carbonate with 900 g deionized water, was poured into the Einlehner test cylinder. Einlehner PVC tubing was placed onto the agitating shaft. The PVC tubing has 5 numbered positions. For each test, the position of the PVC tubing is incremented until it has been used five times, then discarded. The Einlehner abrasion instrument is reassembled and the instrument set to run for 87,000 revolutions. Each test takes about 49 minutes. After the cycle is completed, the screen is removed rinsed in tap water, placed in a beaker containing water and set in an ultrasonic bath for 2 minutes, rinsed with deionized water and dried in an oven set at 105° C. for 20 minutes. The dried screen is cooled in a desiccator and reweighed. Two tests are run for each sample and the results are averaged and expressed in mg lost per 100,000 revolutions. The result, measured in units of mg lost per 100,000 revolutions, for a 10% slurry can be characterized as the 10% brass Einlehner (BE) abrasion value.

The iron and manganese content were determined from an acid solubilized sample using a Perkin-Elmer Model Optima 3000 Inductively Coupled Plasma Spectrophotometer, the operation of which is within the skill of a person of ordinary skill in the art.

The calcium carbonate material prepared according to examples 1–7 and comparative examples 1 and 2 were tested according to the aforementioned test methods. The values obtained for these properties are set forth in Table II, below. For comparative purposes, the properties of a prior art scalenohedral PCC material obtained from Quimica Industrial Barra Do Pirai Ltda., Arcos, Brazil, was also tested.

TABLE II

Physical Properties of Calcium Carbonate

| Example | Aggregate Size, μm | Primary Particle Size, μm | Brass Einlehner (mg loss) | $Fe_2O_3$ ppm | Mn ppm | Lime Source |
|---|---|---|---|---|---|---|
| Ex 1 SEM | 9.1 | 1.0–2.0 | 14.6 | — | — | Itau |
| Ex. 2 | 7.4 | 2–4 | 13.3 | 398 | 56 | Beachville |
| Ex. 3 | 9.3 | 2–4 | 15.1 | 125 | 28 | Itau |
| Ex. 4 | 7.2 | 1.5 | 10.0 | — | — | Itau |
| Ex. 5 | 4.0 | 2–3 | 9.0 | — | — | Itau |
| Ex. 6 | 6.5 | 1.5–3 | 12.4 | — | — | Itau |
| Ex. 7 | 5.2 | 2–3 | 10.4 | — | — | Itau |
| Comp. Ex. 1 | 9.1 | 7–9 | 18.1 | 1100 | 65 | Beachville |
| Comp Ex. 2 | 1.7 | 0.3–1 | 1.0 | 402 | 57 | Beachville |
| Commercial S-PCC | 3.9 | 0.5–1.5 | 3.0 | — | — | — |

The PCC made in Example 2 and Comparative Example 1 was light yellow in color; the remaining examples and comparative examples were white in color. It is believed that the relatively high iron content of Beachville lime contributed to the yellow color for PCC precipitated at pH 8–9.

To demonstrate their efficacy in consumer products, the c-PCC abrasives of Examples 1–3 and 5–7 were incorporated as powders into toothpaste compositions 1–6, set forth below in Table III. The performance of these compositions was then compared with the performance of toothpaste compositions 7–9, which contain prior art calcium carbonates, and are set forth in Table IV, below. The amounts listed in Tables III and IV, below are given in grams.

TABLE III

Toothpaste Compositions Containing PCC prepared according to present invention

| | Toothpaste Composition No. | | | | | |
|---|---|---|---|---|---|---|
| | 1 | 2 | 3 | 4 | 5 | 6 |
| Sorbitol, 70.0%, g | 23.000 | 23.000 | 23.000 | 23.000 | 23.000 | 23.000 |
| Deionized Water, g | 30.800 | 31.200 | 30.800 | 30.800 | 30.800 | 30.800 |
| CMC-7MXF, g | 1.400 | 1.000 | 1.400 | 1.400 | 1.400 | 1.400 |
| Sodium Saccharin, g | 0.300 | 0.300 | 0.300 | 0.300 | 0.300 | 0.300 |

TABLE III-continued

Toothpaste Compositions Containing
PCC prepared according to present invention

| | Toothpaste Composition No. | | | | | |
|---|---|---|---|---|---|---|
| | 1 | 2 | 3 | 4 | 5 | 6 |
| Sodium Monofluorophosphate, g | 0.800 | 0.800 | 0.800 | 0.800 | 0.800 | 0.800 |
| Sodium Silicate, g | 0.900 | 0.900 | 0.900 | 0.900 | 0.900 | 0.900 |
| Abrasive | | | | | | |
| Example 1 | 40.000 | 0.000 | 0.000 | 0.000 | 0.000 | 0.000 |
| Example 2 | 0.000 | 40.00 | 0.000 | 0.000 | 0.000 | 0.000 |
| Example 3 | 0.000 | 0.000 | 40.00 | 0.000 | 0.000 | 0.000 |
| Example 5 | 0.000 | 0.000 | 0.000 | 40.000 | 0.000 | 0.000 |
| Example 6 | 0.000 | 0.000 | 0.000 | 0.000 | 40.00 | 0.000 |
| Example 7 | 0.000 | 0.000 | 0.000 | 0.000 | 0.000 | 40.00 |
| Sodium Lauryl Sulfate, g | 1.800 | 1.800 | 1.800 | 1.800 | 1.800 | 1.800 |
| Flavor, g | 1.000 | 1.000 | 1.000 | 1.000 | 1.000 | 1.000 |

TABLE IV

Toothpaste Compositions Containing
PCC Prepared According to Prior Art

| | 7 | 8 | 9 |
|---|---|---|---|
| Sorbitol, 70.0%, g | 23.000 | 23.000 | 23.000 |
| Deionized Water, g | 31.200 | 31.200 | 30.800 |
| CMC-7MXF, g | 1.000 | 1.000 | 1.400 |
| Sodium Saccharin, g | 0.300 | 0.300 | 0.300 |
| Sodium Monofluorophosphate, g | 0.800 | 0.800 | 0.800 |
| Sodium Silicate, g | 0.900 | 0.900 | 0.900 |
| Abrasive | | | |
| Comparative Example 1 | 40.000 | 0.000 | 0.000 |
| Comparative Example 2 | 0.000 | 40.000 | 0.000 |
| Commercial s-PCC | 0.000 | 0.000 | 40.000 |
| Sodium Lauryl Sulfate | 1.800 | 1.800 | 1.800 |
| Flavor | 1.000 | 1.000 | 1.000 |

After toothpaste compositions 1–9 were prepared as above, properties relating to the performance of the toothpaste, such as viscosity, RDA and PCR were measured and determined as follows.

The RDA is measured by the method described in the article "The Measurement of the Abrasion of Human Teeth by Dentifrice Abrasives: A Test Utilizing Radioactive Teeth", Grabenstetter, R. J.; Broge, R. W.; Jackson, F. L.; and Radike, A. W. in the *Journal of Dental Research*: 37, 1060–68, 1958.

The PCR test is described in "*In Vitro Removal of Stain With Dentifrice*" G. K. Stookey, et al., J. Dental Res., 61, 1236–9, 1982.

A Brookfield viscometer (Model RVT) with a Helipath stand and spindle T-E is used to determine toothpaste viscosity. The viscometer speed is set at 5 rpm. The toothpaste sample container is placed in a water bath set to 25° C. to equilibrate. The viscosity is read at three levels and averaged. Results are reported in centipoise (cps).

The results of the PCR, RDA and viscosity measurements are set forth in Table V, below.

TABLE V

Toothpaste Compositions Performance

| Toothpaste Composition No. | Abrasive | RDA | PCR | Viscosity @ 6 weeks Cps |
|---|---|---|---|---|
| 1 | Example 1 | 122 | 114 | 490,000 |
| 2 | Example 2 | 139 | 135 | 200,000 |
| 3 | Example 3 | 151 | 110 | 460,000 |
| 4 | Example 5 | 88 | 112 | 230,000 |
| 5 | Example 6 | 112 | 114 | 220,000 |
| 6 | Example 7 | 100 | 114 | 390,000 |
| 7 | Comparative Example 1 | 181 | 110 | 130,000 |
| 8 | Comparative Example 2 | 23 | 48 | 570,000 |
| 9 | Commercial s-PCC | 81 | 99 | 1,010,000 |

The toothpaste compositions 1–6 contain calcium carbonate abrasive in which the primary size is from about 1 μm to about 4 μm, while the aggregate particle size is from about 3 μm to about 10 μm. It is seen from the data in Table V that every one of the toothpaste compositions containing the inventive calcium carbonates of Examples 1–3 and 5–7 gave the excellent cleaning results (PCR) without excessive abrasion (RDA) values. By contrast, the toothpastes containing prior art calcium carbonates either: (1) delivered acceptable cleaning performance but were extremely abrasive (RDA) (toothpaste composition 1 containing comparative example 1) or (2) avoided excessive abrasion but at the cost of providing virtually no cleaning benefits (toothpaste composition 8 containing comparative example 2 s-PCC). Toothpaste composition 9 made from a prior art commercial s-PCC having a very small particle size did provide adequate cleaning (although inferior to the cleaning provided by the toothpaste compositions containing PCC prepared according to the present invention) without being excessively abrasive. However, because of the very small size of the particles of the commercial s-PCC, the s-PCC provides unacceptably high viscosity build, resulting in a toothpaste composition that is so viscous it is unacceptable for consumer usage.

Indeed while all of the toothpaste compositions containing PCC prepared according to the present invention provided good dentifrice performance, toothpaste compositions 2, 4, 5, and 6 containing calcium carbonate prepared according to examples 2, 5, 6, and 7, respectively, provided exceptional dentifrice performance as they not only demonstrated excellent dental cleaning, but were also relatively mild to teeth surfaces. The superior performance of toothpaste composition 2 containing the calcium carbonate of example 2 is attributed to the combination of primary particle size and aggregate particle size within a specific range. Likewise, the superior performance provided by the PCCs of examples 5, 6, and 7 is because these calcium carbonate abrasive materials have been milled and so have an aggregate size within a specific size range. The importance of the combination of primary particle size and aggregate size is best illustrated by comparing the RDA and PCR of toothpaste composition 3 containing the calcium carbonate of example 3 to the RDA and PCR of toothpaste compositions 4, 5, 6, containing calcium carbonates prepared according to examples 5, 6, and 7. The calcium carbonate of examples 5–7 were obtained by reducing the aggregate size (by bead milling) of the Example 3 abrasive. By reducing the aggregate size, the RDA (abrasiveness) was significantly reduced while the cleaning performance, PCR, was maintained at effective cleaning levels. This is shown below in Table VI.

TABLE VI

|  | RDA | PCR | Aggregate Size, μm | Particle Size, μm |
|---|---|---|---|---|
| Example 3-unmilled PCC (Toothpaste No. 3) | 151 | 110 | 9.3 | 2–4 |
| Example 5 (Toothpaste No. 4) | 88 | 112 | 4.0 | 2–3 |
| Example 6 (Toothpaste No. 5) | 112 | 114 | 6.5 | 1.5–3 |
| Example 7 (Toothpaste No. 6) | 100 | 114 | 5.2 | 2–3 |

As can be seen in Table VI, when the aggregate size of the calcium carbonate material of example 3 was reduced from 9.3 to between 4–6.5, the resulting RDA was significantly reduced from 151 to between 88 and 112, while the PCR value was maintained. The particle size for all of these materials was relatively similar.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An abrasive, precipitated cubic calcium carbonate having a primary particle size of about 1 μm to about 4 μm, an aggregate size of about 3 μm to about 10 μm, and a Brass Einlehner abrasion value of between about 8 mg loss/100,000 rev. to about 15 mg loss/100,000 rev.

2. A dentifrice comprising the calcium carbonate of claim 1.

3. A dentifrice comprising from about 30 wt% to about 50 wt% base on the weight of the dentifrice of the calcium carbonate according of claim 1.

4. The dentifrice according to claim 3, wherein the dentifrice has a RDA of about 80 to about 150.

5. The dentifrice according to claim 3, wherein the dentifrice has a PCR of greater than about 100.

6. The dentifrice according to claim 3, wherein the dentifrice has a viscosity of less than, about 500,000 CPS.

7. A method for forming calcium carbonate comprising the steps of:
   providing a reactor vessel containing a reaction medium;
   simultaneously introducing carbon dioxide and an aqueous calcium hydroxide slurry into the reaction medium to form calcium carbonate by a precipitation reaction, while maintaining the reaction medium within a pH range of 1 pH unit during the precipitation reaction, wherein the pH range is between about 8 to about 12; and
   milling the calcium carbonate to an aggregate size of about 3 μm to about 10 μm.

8. The method according to claim 7, further comprising a drying step, wherein the milling step occurs subsequent to the drying step.

9. The method according to claim 7, further comprising a drying step, wherein the milling step occurs before the drying step.

10. A dentifrice comprising:
   an abrasive, precipitated calcium carbonate having a primary particle size of about 1 μm to about 4 μm, and an aggregate size of about 3 μm to about 10 μm; and
   one or more ingredients selected from the group consisting of humectants, thickening agents, binders, gums, stabilizing agents antibacterial agents, fluorides, sweeteners, and surfactants.

11. A dentifrice according to claim 10, wherein the dentifrice is in the form of a toothpaste.

* * * * *